US006997933B2

(12) United States Patent
Bittar (10) Patent No.: US 6,997,933 B2
(45) Date of Patent: Feb. 14, 2006

(54) MENISCUS AND SOFT TISSUE REPAIR DEVICE AND METHOD OF USE

(76) Inventor: Edward S. Bittar, 650 S. Riverside Dr., Indialantic, FL (US) 32903

( * ) Notice: Subject to any disclaimer, the term of this patent is extended or adjusted under 35 U.S.C. 154(b) by 380 days.

(21) Appl. No.: 10/194,803

(22) Filed: Jul. 12, 2002

(65) Prior Publication Data

US 2003/0204194 A1 Oct. 30, 2003

Related U.S. Application Data

(60) Provisional application No. 60/375,338, filed on Apr. 26, 2002.

(51) Int. Cl.
*A61B 17/04* (2006.01)

(52) U.S. Cl. .................................... 606/144; 606/148
(58) Field of Classification Search .......... 606/144–148
See application file for complete search history.

(56) References Cited

U.S. PATENT DOCUMENTS

| | | | | |
|---|---|---|---|---|
| 659,422 A | * | 10/1900 | Shidler | 606/144 |
| 4,244,370 A | * | 1/1981 | Furlow et al. | 606/148 |
| 4,493,323 A | * | 1/1985 | Albright et al. | 606/144 |
| 4,635,637 A | * | 1/1987 | Schreiber | 606/219 |
| 5,269,783 A | * | 12/1993 | Sander | 606/72 |
| 5,374,268 A | * | 12/1994 | Sander | 606/72 |
| 5,522,844 A | * | 6/1996 | Johnson | 606/232 |
| 5,843,084 A | * | 12/1998 | Hart et al. | 606/77 |
| 6,190,401 B1 | * | 2/2001 | Green et al. | 606/224 |

* cited by examiner

*Primary Examiner*—Gary Jackson
(74) *Attorney, Agent, or Firm*—Roger M. Rathbun (57) ABSTRACT

A device for repairing a meniscus or soft tissue. A needle having a suture strand attached thereto is affixed to the distal end of an introducer. The introducer is adapted to be inserted through a hollow main body to position the needle proximate a damaged portion of the meniscus. At the proximal ends of the introducer and main body, there is a thumb ring and a pair of finger rings that can be manipulated by the user to position the device and to pierce the meniscus with the needle. The needle is frictionally affixed to the introducer and can be removed by the user after piercing the meniscus and the outer skin of the patient. With the device, a pair of needles having a suture strand joining the needles can be inserted through the meniscus and across the damaged area and the strands of the suture affixed together.

21 Claims, 6 Drawing Sheets

MENISCUS AND SOFT TISSUE REPAIR DEVICE AND METHOD OF USE

REFERENCE TO RELATED CASES

The present application is based upon Provisional Application Ser. No. 60/375,338 filed Apr. 26, 2002 and entitled MENISCUS AND SOFT TISSUE REPAIR DEVICE AND METHOD OF USE.

BACKGROUND OF THE INVENTION

The present invention relates to a device for the repair of the soft tissue of a patient, and, more particularly, to a device and method to repair the meniscus of a knee of the patient.

The meniscus is basically a crescent shaped fibrocartilage shock absorber that is located intermediate the femur or thigh bone and the tibia or shin bone and which assists in retaining the bones in place and includes an outside meniscus, that is, the lateral meniscus and the inside meniscus or medial meniscus. The meniscus, when healthy, absorbs the shock between the thigh bone and ankle bone by cushioning and distributing the forces across the joint as well as stabilizing the knee by controlling its rotation.

A rather common injury that can occur to the knee is a tearing of the meniscus and which can occur as a result, for example, of a twisting of the knee. The tear can result in uneven surfaces that irritate the joint and can cause pain and swelling and a catching sensation. The irritation can increase the longer the tear remains in the meniscus and it is therefore necessary to take some action to repair the tear for the wellbeing of the patient.

Accordingly, certain tears of the meniscus can be corrected by surgery, particularly arthroscopic surgery where a fiber optic instrument is utilized to aid the physician in observing the procedure carried out within the patient's knee so as to cause a minimum of trauma and invasion of the knee. With the surgery, the procedure is basically to suture the torn portion of the meniscus to thereby repair the tear and to reconstitute the meniscus back to its original status.

Obviously, even with an arthroscopic instrument, the operation is a difficult, delicate procedure, requiring great skill since it requires the use of a suture or sutures that cross or span the tear and then a knot formed and tightened to bring the individual strands of the suture together so as to pull the separated sides of the tear together. One device that is used in such procedures is a double needle suture that has two needles joined by the suture strand. Both needles are passed in a parallel fashion through the meniscus tissue on one side of the tear and through the meniscus tissue on the other side of the tear. A loop is formed in the in the suture on the surface of the meniscus when both of the needles have passed through the meniscus. The free ends of the suture are finally knotted.

Thus a difficulty of the surgery is to be able to insert the needles carrying the suture and surgically position and insert the needles so as to pierce the meniscus to pass through the tissue of the meniscus as well as the tissue of the meniscus that has been torn apart in order to suture the torn portion back into the desired location. Even with the use of the arthroscope, it is a delicate procedure to actually position the suture so as to pass the needles and the suture strand affixed thereto through the meniscus as well as the torn portion of the meniscus at two locations.

Accordingly, it would be advantageous to have a device that can facilitate the aforedescribed medical procedure to repair and reattach a torn portion of a meniscus by the use of suture strand interposed between two needles to carry out the procedure and to a better method of carrying out the procedure itself.

SUMMARY OF THE INVENTION

Accordingly, the present invention relates to a device and a method to reattach a torn portion of a fibrocartilage meniscus of the knee to the outer rim and base of the meniscus and can be used in the deep recesses of the knee under fiberoptic guidance during arthroscopic surgery and will be specifically described as such, however it will be noted that the present device and method can also be used for the reattachment of other tissue to bone or other soft tissue in areas that are not easily accessible.

With the present invention, however, there is provided a device that facilitates the placement of one or more sutures in the tissue of a patient and the device includes a main body that is a hollow tube that can be strategically located at the desired site where the suture is intended to pierce the tissue. The main body has a distal end that enters the joint or other area of the patient and that distal end is preferably configured to have a smooth rim so as to allow the entry into the patient to be introduced atraumatically. The main body also has a proximal end that has a slightly flared opening. The main body itself can be comprised of a metal, such as stainless steel, or can be a disposable material such as a plastic and it is preferred that the material be malleable so that the shape of the main body can be customized by the user by bending the main body to fit the desired use.

An introducer slidingly fits within the main body and the introducer has a distal end that has a socket to allow a needle to be frictionally interfitted therein and retained to that distal end. The socket also preferably has an elongated slit formed therein at least substantially along the length of the socket so as to allow a suture strand affixed to the needle to conveniently extend outwardly from the socket through the slit. As such, a needle having a suture strand affixed thereto can be fitted and retained onto the socket located at the distal end of the introducer and the introducer can be slid into and through the main body to a position where the distal end of the introducer projects outwardly from the distal end of the main body.

The introducer can be manipulated by some thumb securing means, such as a thumb ring, at the proximal end of the introducer so as to advance the needle to push the needle through the patient's tissue and across the tear in the meniscus and the needle pulled out the far end of the meniscus. In like manner, the proximal end of the main body also has finger securing means such as finger rings, that allow the fingers of the user's hand to hold the main body while advancing or retracting the introducer with the thumb ring. As can therefore be seen, the use of the device can be readily carried out with only one hand, making it particularly suitable for endoscopic surgical techniques.

In the case of dual needles having a suture strand between the needles, the aforedescribed steps can be repeated at another location proximate the tear in the meniscus so that both needles pierce the meniscus and cross the tear. The ends of the suture strands thus pass through the tear in the meniscus and can be tied or in some manner secured together to bring the sides of the tear together in carrying out the repair of the meniscus.

These and other features and advantages of the present invention will become more readily apparent during the following detailed description taken in conjunction with the drawings herein.

DETAILED DESCRIPTION OF THE INVENTION

Figure 1:
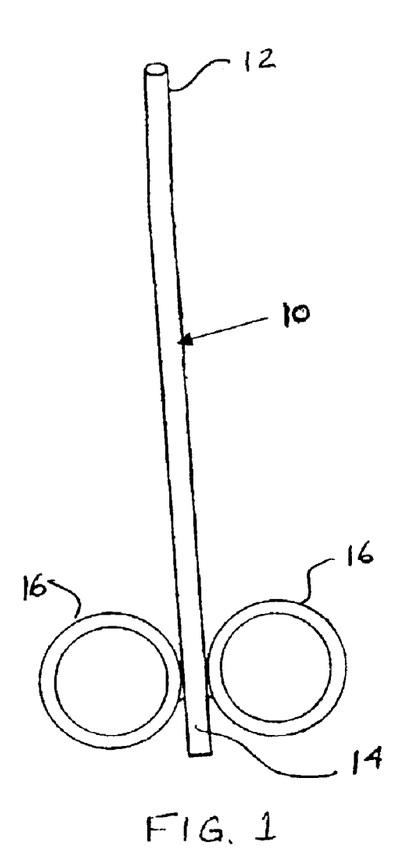
FIG. 1 is front view of the main body component of the present invention.
Figure 2:
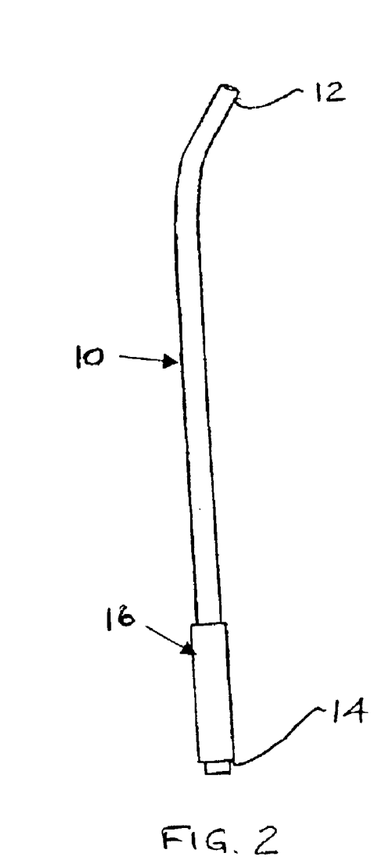
FIG. 2 is a side view of the body component of FIG. 1.

Referring now to FIGS. 1 and 2, there is shown a front view and a side view, respectively, of a meniscus and soft tissue repair device having a main body 10 that is basically a hollow tube with a lumen through the entire main body 10 and which is a component of the present invention. The main body 10 has a distal end 12 that is adapted to be inserted into the patient to be located proximate the area where a suture is to be inserted. As such, the distal end 12 has a smooth rim so that it can be introduced into the joint of the patient atraumatically.

There is also a proximal end 14 that may be slightly flared for a purpose that will later become clear. As also noted, at or near the distal end 12, the main body 10 is curved, however, the main body 10 may also be straight or differently curved in a variety of configurations. The material for the main body 10 can be a rigid material such as stainless steel or some malleable metal or a plastic, it being preferable that the material be somewhat malleable so the user can bend or configure the shape of the main body 10 depending upon the particular application. Thus, the main body 10 can be constructed of a bendable metal or a bendable plastic and be a disposable product after a single use of the device.

There is a also a finger support means located at the proximal end 14 and which is preferably a pair of finger rings 16 that enable the user to slip fingers into the finger rings 16 in carrying out the manipulation of the repair device.

Figure 3:
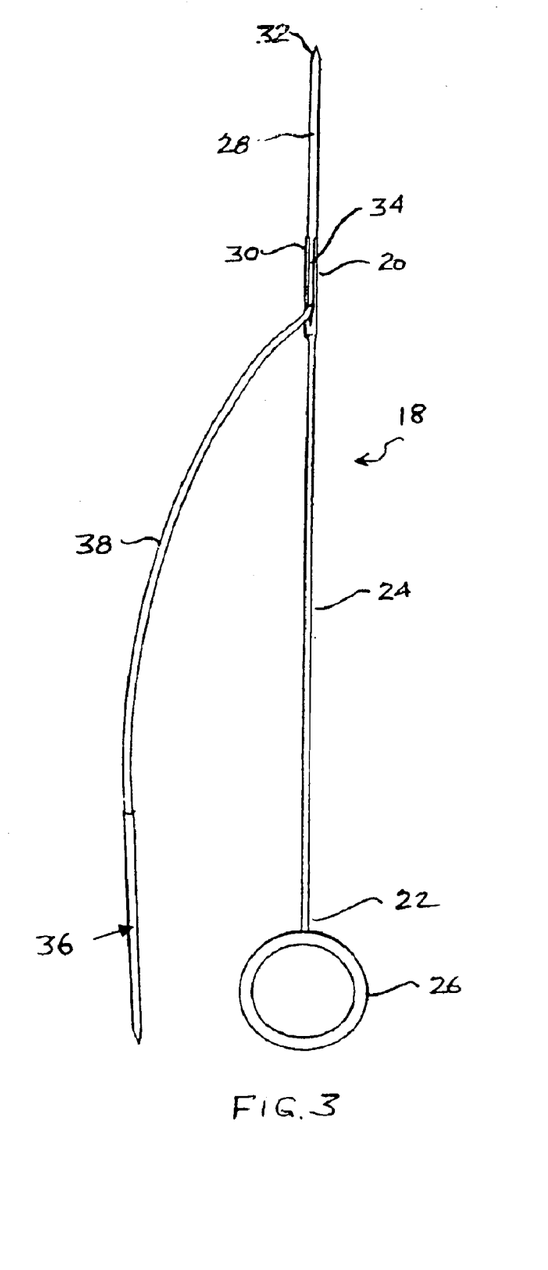
FIG. 3 is a front view of the introducer component of the present invention.
Figure 4:
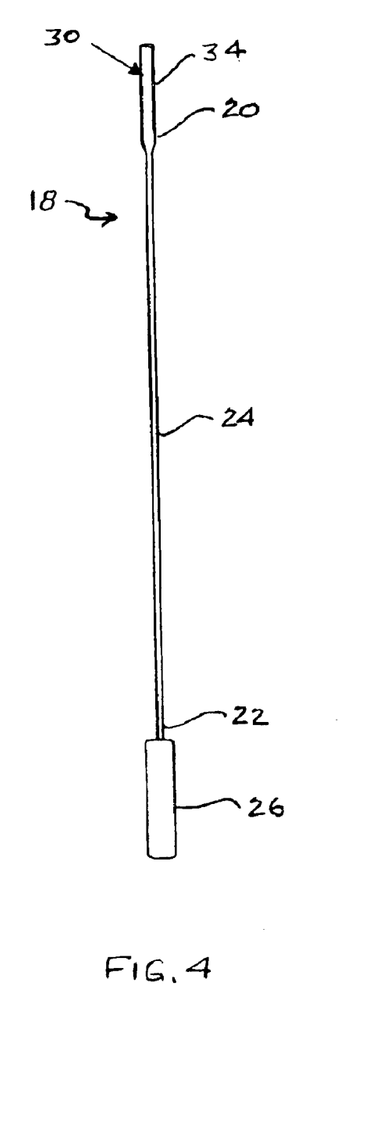
FIG. 4 is a side view of the introducer of FIG. 3.

Turning now to FIGS. 3 and 4, there is shown, a side and an end view of an introducer 18 that is a component of the present invention and functions in cooperation with the main body shown in FIGS. 1 and 2. The introducer 18 has a distal end 20, and a proximal end 22 with a shaft 24 therebetween. The proximal end 22 is provided with a thumb grip, shown as a thumb ring 26 so that the user can insert the thumb in carrying out the manipulation of the repair device.

Again, the shaft 24 can be comprised of various materials, including stainless steel or a malleable metal or plastic and it is preferable that the shaft 24 be relatively flexible so as to slide freely within the main body 10 no matter what the configuration is of that main body 10. (FIGS. 1 and 2). In FIG. 3, there is a needle 28 that is affixed to the distal end 20 of the introducer 18 and thus the distal end 20 has a socket 30 that receives the needle 28 to retain the needle 28 oriented coaxially with the shaft 24 with the point 32 of the needle 28 extending distally from the distal end 20 of the introducer 18.

The socket 30 has an elongated slit 34 that extends at least substantially along the length of the socket 30. In the use of the repair device of the present invention, a double needle is utilized that is joined by a strand of suture and therefore, in FIG. 3, there can be seen a first needle 28 affixed to the distal end 20 of the introducer 18 while there is a second needle 36 and a suture strand 38 therebetween.

Accordingly, the construction of the distal end 20 of the introducer 18 allows the needle 28 to be interfitted within the socket 30 and be frictionally held therein so that the needle 28 can be simply inserted into and pulled out of the socket 30 by the user. By the providing of the elongated slit 34, the suture strand 38 that is affixed to the needle 28 can be threaded through the elongated slit 34 even though the strand 38 remains affixed to the proximal end of the needle 28.

Figure 5:
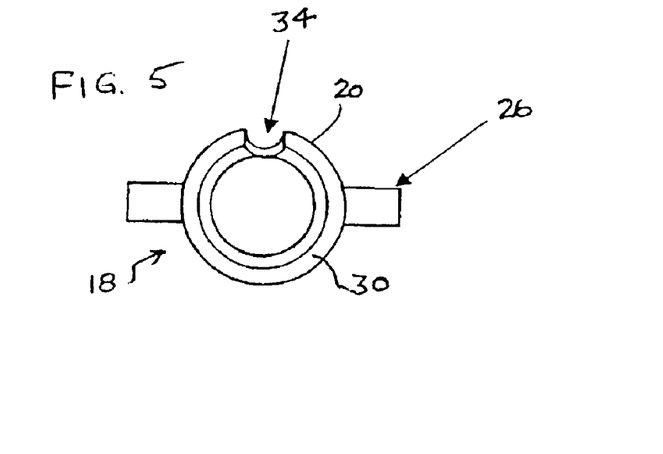
FIG. 5 is an enlarged end view of the distal end of the introducer.
Figure 6:
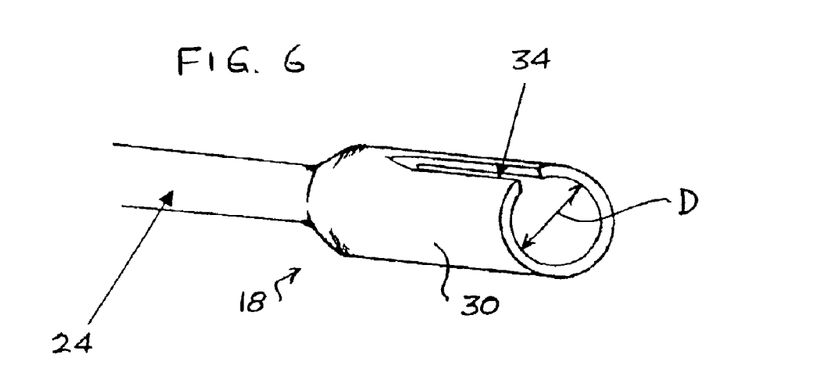
FIG. 6 is a perspective view of the distal end of the introducer.

Turning now to FIGS. 5 and 6, there is shown an end view and a perspective view of the distal end 20 of the introducer 18. In these views, the elongated slit 34 can be better seen and the inner diameter D of the socket 30 is dimensioned so as to create a tight, interference fit with the needle 28 (FIG. 3) so that the needle can be forced into the socket 30 and frictionally retained therein but the needle 28 can also be pulled by the user outwardly to remove the needle from the socket 30.

Figure 7:
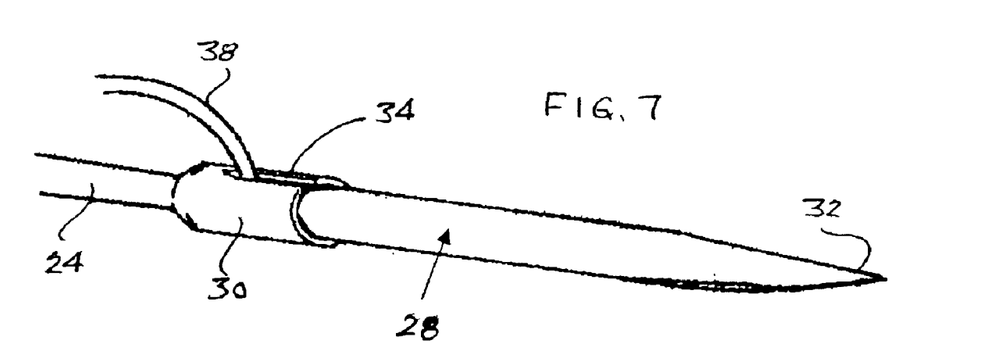
FIG. 7 is an enlarged perspective view of the introducer having a needle affixed thereto.

In FIG. 7, the suture strand 38 can be seen exiting the socket 30 through the use of the elongated slit 34.

Figure 8:
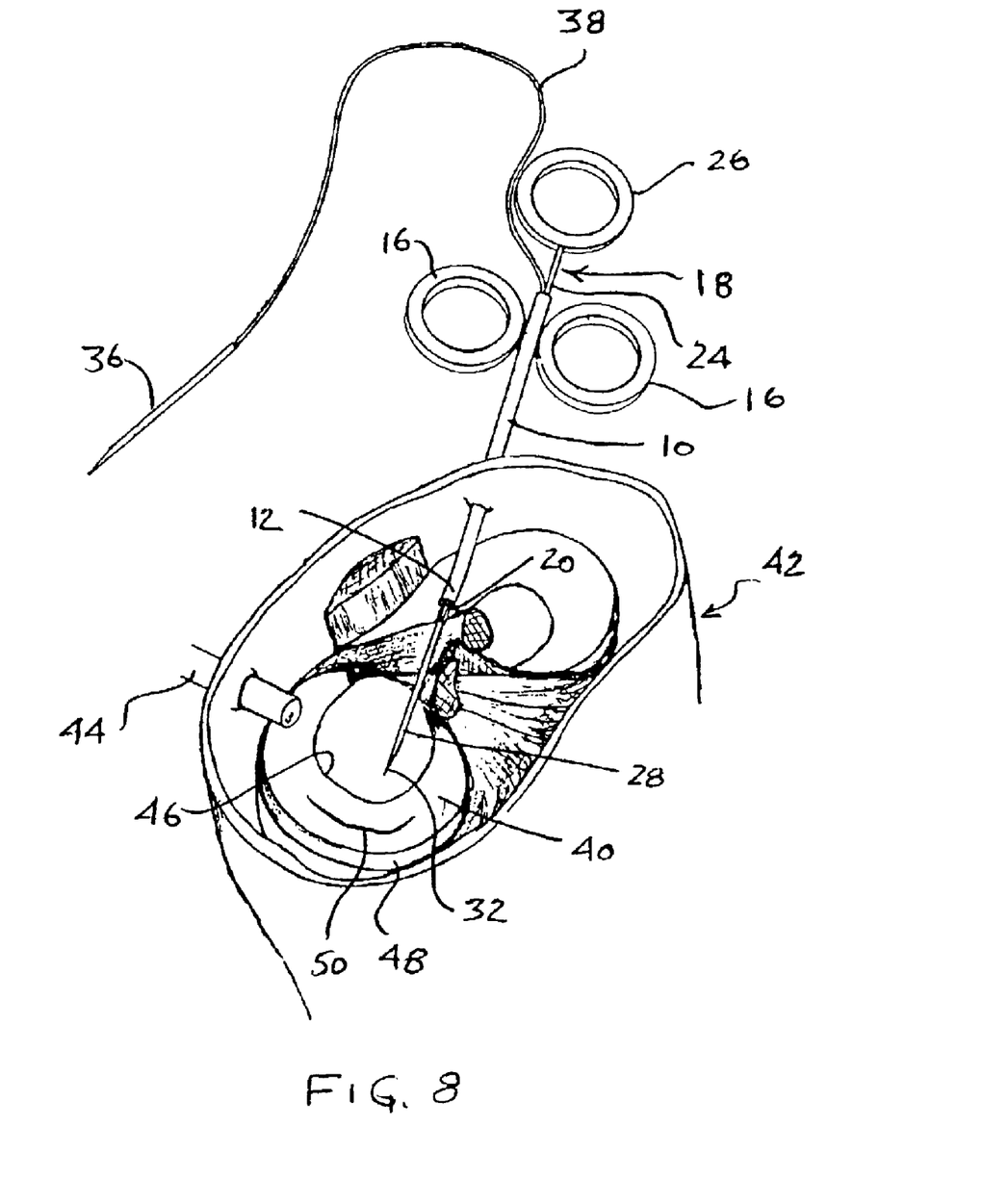
FIG. 8 is a schematic view showing a step in a procedure to repair a tear in a meniscus using the device of the present invention.

Turning to FIGS. 8–12, there are shown schematic views of a medical procedure to carry out the repair of a tear in a meniscus of a patient's knee using the repair device of the present invention. In FIG. 8, the repair device is shown with the introducer 18 slidingly fitted within the main body 10 such that the distal end 20 of the introducer 18 extends beyond the distal end 12 of the main body 10. As also can be seen, the meniscus 40 is located within the knee 42 of a patient and an arthroscope 44 has been positioned proximate the meniscus 40 penetrating the knee 42 in order for the physician to observe and guide the needle 28 as it is used to penetrate the meniscus 40.

Thus, the point 32 of the needle 28 is poised and positioned proximate the inner rim 46 of the meniscus 40 and oriented toward the outer rim 48 so that the suture strand 38 will pass across the tear 50 in the meniscus 40 as a result of the procedure. The second needle 36 remains at the other end of the suture strand 38 and the suture strand 38 itself is threaded, along with the shaft 24 of the introducer 18 through the hollow lumen of the main body 10. As also can be seen, the user can insert the thumb through the thumb ring 26 and insert two fingers through the finger rings 16 to manipulate the introducer 18, and thereby the needle 28, much in the same manner as a syringe, with the use of only one hand.

Figure 9:
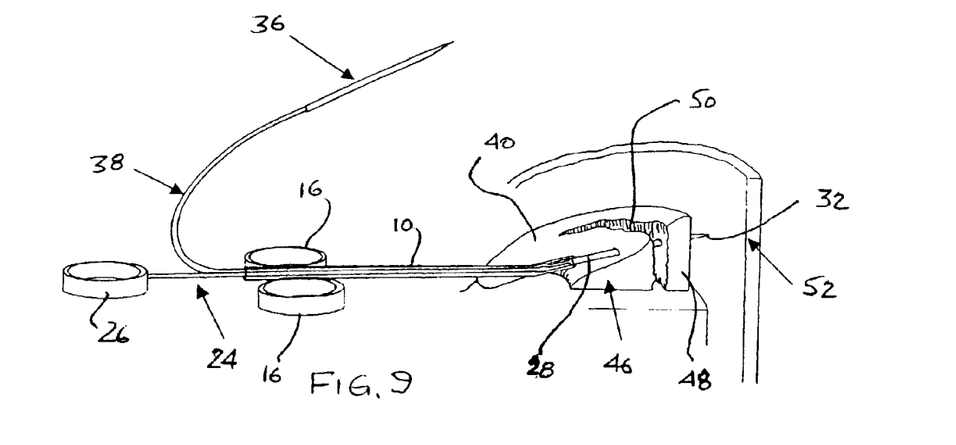
FIG. 9 is a schematic view of a further step in the procedure of FIG. 8.

In the schematic of FIG. 9, the needle 28 has penetrated the meniscus 40 and has passed through the inner rim 46 and the outer rim 48 of the meniscus 40 passing across the tear 50 and the point 32 of the needle is still, however, interior of the outer skin 52 of the patient.

Figure 10:
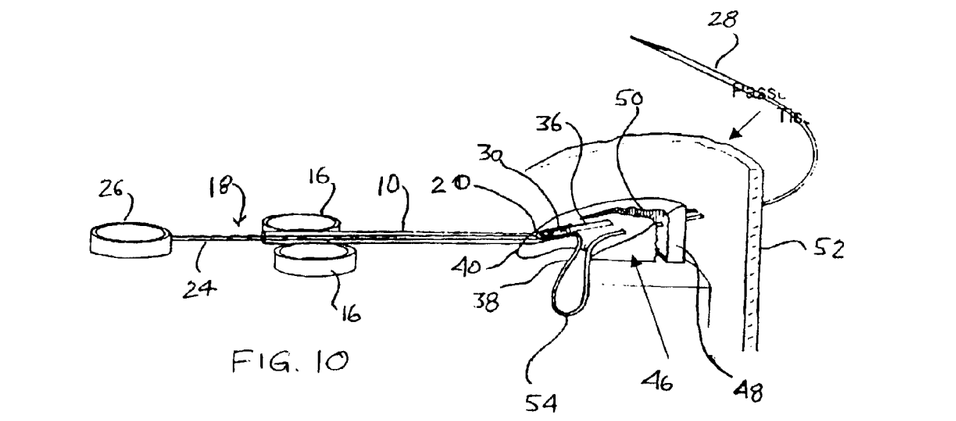
FIG. 10 is a schematic view of a further step in the procedure of FIG. 8.

Next, in the schematic view of FIG. 10, the first needle 28 has passed completely through the outer skin 52 and has been pulled by the user from the socket 30 at the distal end 20 of the introducer 18. Thus, the introducer 18 has, in the interim, been removed from the main body 10 and the second needle 36 affixed into the socket 30 at the distal end 20 of the introducer 18 and the introducer 18 again inserted into the main body 10 to the position as shown in FIG. 10.

Accordingly, there is a loop 54 that is formed in the suture strand 38 between the first and second needles 28, 36 and the second needle 36 has penetrated the inner rim 46 and the outer rim 48 of the meniscus 40 passing across the tear 50 by a manipulation of the thumb ring 26 and the finger rings 16 by a hand of the user.

Figure 11:
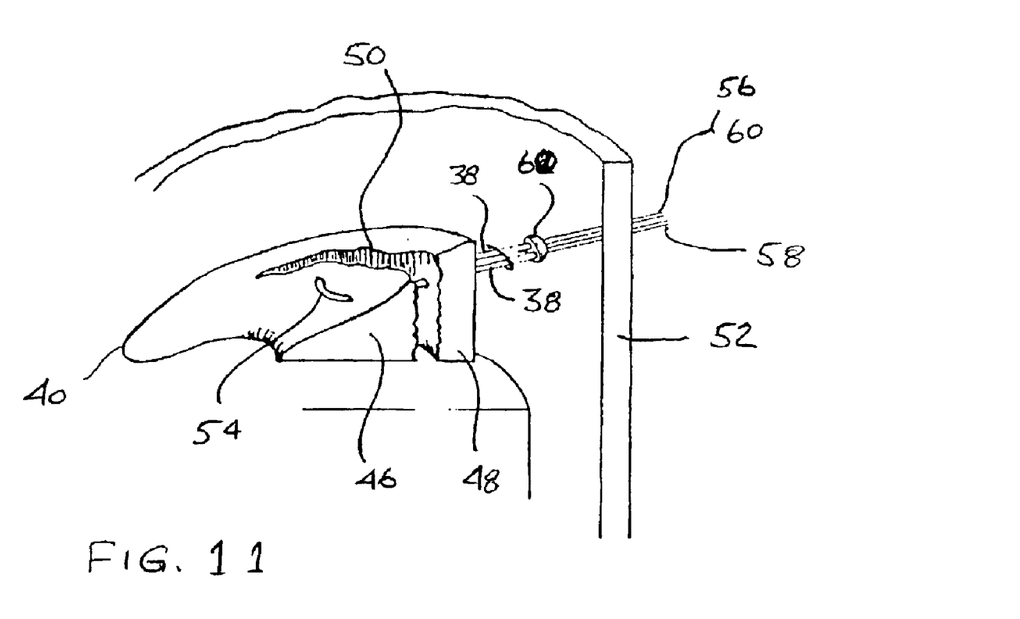
FIG. 11 is a schematic view of a further step in the procedure of FIG. 8.

In the schematic of FIG. 11, the procedure has continued and, at this point, the second needle 36 had pierced the outer skin 52 and been removed by the user and the introducer 18 and the outer body 10 removed from the patient. As such, the loop 54 of the suture strand 38 has secured the inner rim 46 of the meniscus 40 and both of the free ends 56, 58 of the suture strand 38 are located external of the outer skin 52 of a patient.

A plug 50 having two holes is positioned with both of the suture strands 38 passing through those holes and the plug 60 is slid along the suture strands 38 as tension is applied to those strands 38 such that the plug 60 can be seated onto the outer surface of the outer rim 48 of the meniscus 40. At that point, the suture strands 38 can be tied together by the user to seat the plug 60 and pull the inner and outer rims 46, 48 together. As an alternative to tying a knot in the ends of the strands 38, those strands can, of course, be welded together or affixed by other means.

Figure 12:
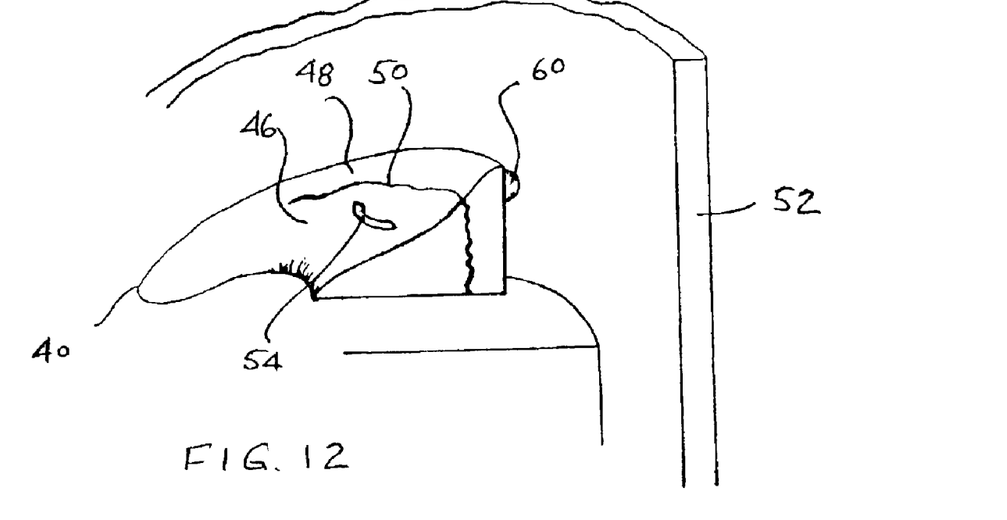
FIG. 12 is a schematic view of a further step in the procedure of FIG. 8.

Finally, in FIG. 12, there is shown a schematic view of the completed repair of the tear 50 and illustrating the location of the plug 60 tightly seated against the meniscus 40 with the inner and outer rims 46, 48 brought together and secured in that position bring the sections of the tear 50 together.

Those skilled in the art will readily recognize numerous adaptations and modifications which can be made to the meniscus and soft tissue repair device and method of using the same of the present invention which will result in an improved process and device, yet all of which will fall within the scope and spirit of the present invention as defined in the following claims. Accordingly, the invention is to be limited only by the following claims and their equivalents.

I claim:

1. A device for the piercing of a single shaft needle having a suture strand affixed thereto through a patient's tissue, said device comprising a main body having a distal end, a proximal end and a passageway therethrough, an introducer adapted to pass through said passageway of said main body, said introducer having a distal end and a proximal end, said distal end of said introducer having a cylindrical socket formed therein configured to axially receive and releasably retain a single shaft needle within said socket, said distal end of said introducer adapted to extend outwardly from the distal end of said main body when said introducer is within said passageway, and a means located at the proximal ends of said introducer and said main body to enable a user to grasp and manipulate the movement of said introducer within said main body to pierce the tissue of the patient with a single shaft needle.

2. A device as defined in claim 1 wherein said distal end of said main body is a smooth, cylindrical rim to enable said main body to be introduced atraumatically into a patient.

3. A device as defined in claim 1 wherein said main body is malleable so as to be bendable into differing shapes.

4. A device as defined in claim 1 wherein said cylindrical socket is formed to frictionally engage a single shaft needle.

5. A device as defined in claim 1 wherein said means located at the proximal end of said introducer to enable a user to grasp and manipulate the introducer comprises a thumb ring.

6. A device as defined in claim 5 wherein said means located at the proximal end of said main body to enable a user to grasp and manipulate the introducer comprises a pair of finger rings.

7. A device as defined in claim 1 wherein said proximal end of said main body is flared to allow easy entry of the introducer.

8. A device as defined in claim 6 wherein said socket is dimensioned to receive and retain a single shaft needle by frictional engagement.

9. A device as defined in claim 1 wherein said socket has a slit formed therein along at least substantially the length of said socket to allow a suture strand to extend outwardly from the slit when a single shaft needle is fitted within said socket.

10. A device as defined in claim 1 wherein said main body is a malleable material constructed of a plastic or metal material.

11. A method of passing a single shaft needle having a suture strand affixed to one end of a single shaft needle through the tissue of a patient, said method comprising the steps of:

providing a hollow, cylindrical elongated main body having a distal end and a proximal end, providing an introducer having a distal end having a cylindrical socket and a proximal end and adapted to interfit within the hollow elongated main body, affixing a single shaft needle to the cylindrical socket at the distal end of the introducer;

inserting the introducer through the main body such that the distal end retaining the single shaft needle extends outwardly from the distal end of the main body, extending the introducer to pass the single shaft needle through the tissue of a patient by manipulating the proximal ends of the introducer and the main body with respect to each other, removing the single shaft needle from the cylindrical socket at the distal end of the introducer after the single shaft needle has passed through the tissue of a patient.

12. A method as defined in claim 11 wherein said step of extending the introducer comprises pushing the proximal end of the introducer inwardly with respect to the main body.

13. A method as defined in claim 11 wherein said step of providing an introducer comprises providing an introducer having a means at the proximal end to retain a finger of a user.

14. A method as defined in claim 11 wherein said step of affixing a single shaft needle to the introducer comprises frictionally engaging a single shaft needle within the cylindrical socket.

15. A method as defined in claim 14 wherein said step of providing an introducer having a socket at the distal end comprises providing a socket having a slit formed in the socket along at least substantially the length of the socket.

16. A method as defined in claim 15 wherein said step affixing a needle to the distal end of the introducer comprises threading the suture strand affixed to the single shaft needle outwardly through the slit in the socket.

17. A method of repairing a tear in the tissue of a patient by passing a first and second needle having a suture affixed between the needles through the tissue of a patient, said method comprising the steps of:

(a) providing a hollow elongated main body having a distal end and a proximal end, (b) providing a introducer having a distal end and a proximal end and adapted to interfit within the hollow elongated main body, (c) affixing the one of said needles to the distal end of the introducer;

(d) inserting the introducer through the main body such that the distal end retaining the needle extends outwardly from the distal end of the main body, (e) extending the introducer to pass the needle through the tissue of a patient by manipulating the proximal ends of the introducer and the main body with respect to each other, (f) removing the needle from the distal end of the needle after the needle has passed through the tissue of a patient, (g) repeating steps (a) through (f) with the other of the needles; and (h) securing together the ends of the suture strands joined to each of said needles to close the tear in a patient's tissue.

18. A method as defined in claim 17 wherein said step of securing the ends of the suture strands together comprises tying a knot in the suture strands.

19. A method as defined in claim 17 wherein said step of providing an introducer comprises providing an introducer having a socket at the distal end thereof and said step of affixing a needle to the introducer comprises frictionally engaging a needle within the socket.

20. A method as defined in claim 17 wherein said step of providing an introducer having a socket at the distal end comprises providing a socket having a slit formed in the socket along at least substantially the length of the socket.

21. A method as defined in claim 17 wherein said step of securing the ends of the suture strands together comprises welding the ends of the suture strands together.

* * * * *